(12) United States Patent
Carchidi et al.

(10) Patent No.: US 6,454,567 B1
(45) Date of Patent: Sep. 24, 2002

(54) DENTAL IMPLANT DELIVERY AND DRIVE TOOL

(75) Inventors: Joseph Edward Carchidi, West Bridgewater, MA (US); Alan R. Balfour, Petaluma, CA (US)

(73) Assignee: ACE Surgical Supply Co., Inc., Brockton, MA (US)

( * ) Notice: Subject to any disclaimer, the term of this patent is extended or adjusted under 35 U.S.C. 154(b) by 0 days.

(21) Appl. No.: 09/841,532

(22) Filed: Apr. 23, 2001

(51) Int. Cl.⁷ .................................................. A61C 3/00
(52) U.S. Cl. ........................................ 433/141; 433/174
(58) Field of Search ................. 433/141, 173, 433/174

(56) References Cited

U.S. PATENT DOCUMENTS

| | | | |
|---|---|---|---|
| 4,202,244 A | | 5/1980 | Gutshall |
| 4,995,810 A | * | 2/1991 | Soderberg .................... 433/141 |
| 5,105,690 A | | 4/1992 | Lazzara |
| 5,312,254 A | * | 5/1994 | Rosenlicht .................. 433/173 |
| 5,322,443 A | * | 6/1994 | Beaty .......................... 433/141 |
| 5,409,377 A | * | 4/1995 | Mays .......................... 433/220 |
| 5,538,428 A | | 7/1996 | Staubli |
| 5,636,990 A | * | 6/1997 | Stemmann ................... 433/189 |
| 5,690,489 A | | 11/1997 | Carchidi |
| 5,944,525 A | * | 8/1999 | Ura .............................. 433/173 |
| 6,068,480 A | * | 5/2000 | Misch et al. ................. 433/173 |
| 6,159,008 A | * | 12/2000 | Kumar ........................ 433/163 |
| 6,203,323 B1 | * | 3/2001 | Beaty et al. ................. 433/173 |
| 6,217,332 B1 | * | 4/2001 | Kumar ....................... 433/173 |
| 6,247,932 B1 | * | 6/2001 | Sutter ......................... 433/173 |
| 6,261,097 B1 | * | 7/2001 | Schmutz et al. ............ 433/173 |

* cited by examiner

*Primary Examiner*—Ralph A. Lewis
(74) *Attorney, Agent, or Firm*—John A. Haug

(57) ABSTRACT

A combined internal polygonal and locking drive tool (10, 10') used to engage a mating external implant mounting and drive fixture (12). The locking drive has an internal tapered locking drive section (10b) which is longitudinally in series with an internal polygonal section (10d) and has its largest diameter slightly larger than the smallest diameter of the internal polygonal portion. The combined delivery and drive tool can be incorporated with an external hand drive or power drill drive surface configuration.

7 Claims, 1 Drawing Sheet

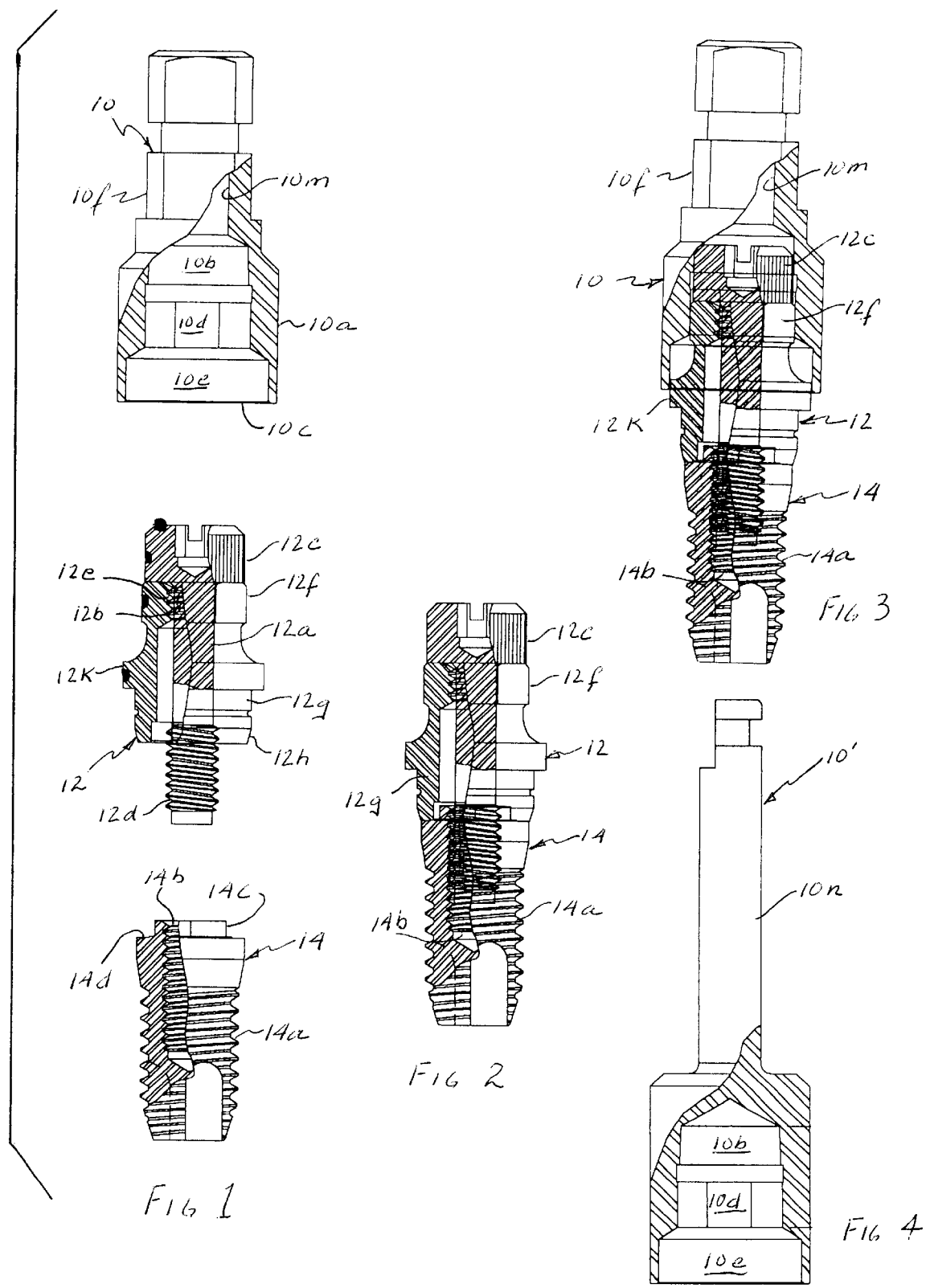

DENTAL IMPLANT DELIVERY AND DRIVE TOOL

FIELD OF THE INVENTION

This invention relates generally to surgical and prosthetic tools and more particularly to such tools used to deliver and insert, by means of rotational torque, dental implants and related components without having to touch and risk contamination of the implants and related components.

BACKGROUND OF THE INVENTION

It is common to provide dental implants with an external thread for threading into an osteotomy. To insert such implants, a fixture mounting drive tool is used to engage and drive a polygonal drive feature on the implant. This fixture mounting drive tool is driven with rotational torque, either by a hand or power drive tool. It is a conventional procedure to assemble the drive portion of the tool with the fixture mounting portion of the tool without having to touch or contaminate the surgical implant components using a tool which incorporates either a spring or an O-ring inside the drive mechanism to secure the fixture mounting drive tool during its rotary drive procedure and insertion of the surgical device. Although this type of tool performs the desired function of inserting a surgical device into the desired surgical site, the continuous use of such tool tends over time to either wear or fracture the internal spring or O-ring inside the tool. Furthermore, since these tools are made from multiple components and require assembly, they are subject to uncontrolled variations in their fit as well as being relatively costly to produce. Additionally, since these drive tools are frequently used for insertion of dental implants between adjacent dentition, having a drive tool whose outer diameter is minimized is desired. Accomplishing this desired size minimization with a multi component tool involves additional design and manufacturing challenges, adding to cost and adversely affecting reliability.

SUMMARY OF THE INVENTION

It is an object of the present invention to provide a tool which overcomes the above noted limitations of the prior art. Another object of the invention is the provision of a tool which locks onto an implant fixture mount and concomitantly an implant which can be driven by a hand or by a power tool, threading the implant into a predefined osteotomy. Yet another object of the invention is the provision of a tool which is formed as a single component not requiring the retention springs or O-rings of the prior art which jeopardize the functional predictability of the tool and which are more costly to produce. Still another object of the invention is the provision of a tool that meets size requirements conducive for placement of an implant between adjacent dentition in the oral cavity.

Briefly, in accordance with the invention, a single component tool has a body having a longitudinal axis and formed with a cavity therein open at its bottom end and provided with a polygonal feature defining the side wall of a section of the cavity. The side wall of another section of the cavity is formed with a frictional locking taper longitudinally in series and in spatial communication with the polygonal feature and in the preferred embodiment, further removed from the bottom end of the body than the polygonal section. The largest diameter of the tapered section is selected to be slightly smaller than the smallest diameter of the internal polygonal so that both a friction locking engagement of a mating cylindrical surface for delivery and a polygonal engagement for driving of a mating polygonal surface can be achieved.

Additional objects and features of the invention will be set forth in part in the description which follows and in part will be obvious from the description. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of the specification, illustrate a preferred embodiment of the invention and together with the description, serve to explain the objects, advantages and principles of the invention. In the drawings:

FIG. 1 is an exploded front elevational view, partly in cross section, of a dental implant, an implant mounting fixture and a hand drive tool made in accordance with the invention, FIG. 2 is front elevational view, partly in cross section, of the FIG. 1 dental implant and implant mounting fixture shown with the dental implant attached to the implant mounting fixture, FIG. 3 is a front elevational view, partly in cross section and similar to FIG. 2, but shown with the implant mounting fixture and dental implant attached to the drive tool shown in FIG. 1, and FIG. 4 is a front elevational view, partly in cross section, of a power drill drive tool useful with the dental implant and implant mounting fixture shown in FIG. 2.

DETAILED DESCRIPTION OF PREFERRED EMBODIMENTS

FIG. 1 shows a hand drive tool 10 made in accordance with the invention along with an implant mounting fixture 12 and a conventional threaded implant 14. Implant 14 has an external thread 14a for threaded engagement with bone defining an osteotomy, a bore having an internal thread 14b for receipt of a suitable threaded abutment post and a polygonal feature 14c at the coronal end of the implant. Implant mounting fixture 12 comprises a retaining screw 12a having a post with a first threaded section 12b contiguous to cylindrical head 12c and a second threaded section 12d at the distal end of the post. The first threaded section 12b is threadingly received in a threaded bore 12e of a hub having an external polygonal feature 12f and with head 12c bottomed out on the hub. A sleeve 12g extends downwardly from the hub to a distal end portion 12h adapted to seat on the top annular surface 14d of the implant and is provided with a centering and stabilizing circular ring 12k intermediate to the hub and distal end 12h, as will be discussed below. Hand drive tool 10 comprises a cylindrical body portion 10a having a hollow interior or cavity in which is formed a circular, cylindrical section 10b formed along a first longitudinal axial portion and having a friction locking taper with the bore increasing in diameter in the direction of the longitudinal axis going toward open distal or bottom end 10c. A polygonal shaped section 10d is formed along a second longitudinal axial portion, closer to the distal end 10c and preferably spaced from the first longitudinal axial portion. A circular counterbore 10e is formed along a third longitudinal axial portion at the distal end 10c.

Drive tool 10 serves to deliver and drive implant 14 by means of implant mounting fixture 12 which mates with tool 10. Implant 14 is threadingly attached to implant mounting fixture 12 as seen in FIG. 2 with threaded portion 12d of mount 12 threadingly received in threaded bore 14b of implant 14. As seen in FIG. 3, the assembled implant and implant mounting fixture are then inserted into drive tool 10 so that head 12c of mounting fixture 12 is frictionally engaged by the frictional locking section 10b. Friction locking tapered section 10b is placed longitudinally is series with polygonal section 10d to enable the delivery as well as the driving capability of implant 10 using a single component tool. Thus implant 14 can be delivered to a pre-defined osteotomy utilizing the frictional locking feature and driven into place utilizing the polygonal drive feature. A rotational force can be applied to drive tool 10 by means of an external polygonal section 10f, such as a square drive feature. This rotational force is transferred to mounting fixture 12 through polygonal section 10d of the drive tool to polygonal section 12f of mounting fixture 12. The taper of friction locking tapered section 10d is less than approximately 6 degrees and, as noted above, the largest diameter of the tapered section, which is closest to polygonal section 10f, is selected to be slightly smaller than the smallest diameter of the internal polygonal section 10d. When assembled with the mating implant fixture mount 12, the friction locking taper locks onto the circular outer periphery of the head of the mounting fixture's retaining screw 12a for delivery of the unit, while the internal polygonal section 10d mates with the external polygonal feature 12f on mounting fixture 12 to drive the assembly. Counterbore section 10e, adjacent to polygonal drive section 10d of mount 12, mates with centering and stabilizing ring 12k for concentric delivery and insertion to the surgical site. The single component hand drive tool can also incorporate a through hole 10m to allow for access by certain tools to the mounting fixture's retaining screw 12a when access or removal is desired.

External square drive feature 10f can be driven with any standard square drive of ratchet tool. Adjacent to the external square drive feature 10f is cylindrical outer diameter 10a which is selected to be minimized in order to allow for the insertion of the attached implant to a site that is located between adjacent teeth or dentures.

FIG. 4 shows a contra-angle drill shaft tool 10' made in accordance with the invention. In addition to drill shaft 10n for power drills or the like, tool 10' includes the friction locking tapered section 10b longitudinally placed in series with polygonal drive section 10d and counterbore 10e to frictionally lock and drive the centered and stabilized mating assembled implant and fixture mount into a surgical site.

Thus the aforementioned single component hand and contra-angle drill shaft tool provides a cost effective, easy to use tool in accordance with the stated objects of the invention. The single component tool obviates the prior art internal spring and O-ring and can be made with a minimized external profile for use when space is at a premium.

Although the invention has been described with regard to certain preferred embodiments thereof, variations and modifications will become apparent to those skilled in the art. It is, therefore, the intention that the appended claims be interpreted as broadly as possible in view of the prior art to include all such variations and modifications.

What is claimed:

1. A delivery and drive system for a dental implant comprising an implant mounting fixture having a hub having a longitudinal axis and formed with an external polygonal peripheral surface, a threaded bore formed through the hub extending along the longitudinal axis, a retaining screw threadingly received in the threaded bore in the hub, the retaining screw having a generally cylindrical head received on the hub with the retaining screw extending beyond the hub for receipt in a threaded bore of an implant, a delivery and drive tool formed from an elongated body having at least a portion thereof formed with an external cylindrical wall having a top and a bottom portion with a longitudinal axis therebetween and having an opening extending from the bottom portion along the longitudinal axis, a cylindrical, friction locking tapered side wall of the opening formed along a first longitudinal axial length portion, the diameter of the cylindrical wall increasing in the direction going from the top portion toward the bottom portion of the body, a polygonal side wall of the opening formed along a second longitudinal axial length portion closer to the bottom portion of the body, the smallest diameter of the polygonal side wall being slightly larger than the largest diameter of the tapered side wall and a non-circular drive portion formed externally on the elongated body.

2. A delivery and drive system according to claim 1 in which a sleeve extends from the hub of the implant mounting fixture to a seating end of the fixture and an external, radially extending, centering and stabilizing ring is formed on the sleeve of the fixture intermediate to the hub of the fixture and the seating end of the fixture, and a counter bore is formed at the opening of the delivery and drive tool, the counterbore having a diameter selected to closely receive the centering and stabilizing ring if the fixture.

3. A delivery and drive system according to claim 1 in which the non-circular drive portion of the delivery and drive tool is square in a cross section taken therethrough perpendicular to the longitudinal axis to facilitate manual driving of the tool.

4. A delivery and drive system according to claim 3 in which the opening of the delivery and drive tool extends through the top portion of the tool.

5. A delivery and drive system according to claim 1 in which the non-circular drive portion of the delivery and drive tool includes an elongated top portion formed with at least one flat on its peripheral surface to accommodate power drill equipment.

6. A delivery and drive tool system according to claim 1 in which the taper of the friction locking side wall of the implant mounting fixture forms an angle with the longitudinal axis of less than approximately six degrees.

7. A delivery and drive tool formed from an elongated body having at least a portion thereof formed with an external cylindrical wall having a top and a bottom portion with a longitudinal axis therebetween and having an opening extending from the bottom portion along the longitudinal axis, a cylindrical, friction locking tapered side wall of the opening formed along a first longitudinal axial length portion, the tapered side wall forming an angle with the longitudinal axis of less than approximately six degrees, the diameter of the cylindrical wall increasing in the direction going from the top portion toward the bottom portion of the body, a polygonal side wall of the opening formed along a second longitudinal axial length portion closer to the bottom portion of the body and spaced apart from the first longitudinal axial length portion, the smallest diameter of the polygonal side wall being slightly larger than the largest diameter of the tapered side wall and a non-circular drive portion formed externally on the elongated body.

* * * * *